US008499367B2

(12) United States Patent
Almqvist

(10) Patent No.: US 8,499,367 B2
(45) Date of Patent: Aug. 6, 2013

(54) COOLING GARMENT HAVING PHASE CHANGE MATERIAL IN ITS EXTREMITY PORTIONS

(75) Inventor: Hans O. Almqvist, Southbury, CT (US)

(73) Assignee: Createc Consulting, LLC, Southbury, CT (US)

(*) Notice: Subject to any disclaimer, the term of this patent is extended or adjusted under 35 U.S.C. 154(b) by 912 days.

(21) Appl. No.: 11/571,496

(22) PCT Filed: Jul. 1, 2005

(86) PCT No.: PCT/US2005/023449
§ 371 (c)(1),
(2), (4) Date: Apr. 2, 2008

(87) PCT Pub. No.: WO2006/014338
PCT Pub. Date: Feb. 9, 2006

(65) Prior Publication Data
US 2008/0168595 A1    Jul. 17, 2008

Related U.S. Application Data

(63) Continuation-in-part of application No. 11/167,324, filed on Jun. 27, 2005, now abandoned.

(60) Provisional application No. 60/585,519, filed on Jul. 2, 2004.

(51) Int. Cl.
*A62B 17/00* (2006.01)

(52) U.S. Cl.
USPC ............................................................. 2/458

(58) Field of Classification Search
USPC .................. 428/311.11, 312.2, 316.6, 317.9, 428/320.2; 2/2.16, 93, 94, 113–115, 69, 2.11, 2/458, 124, 125
See application file for complete search history.

(56) References Cited

U.S. PATENT DOCUMENTS

| 4,753,241 A | 6/1988 | Brannigan et al. |
| 4,856,294 A * | 8/1989 | Scaringe et al. ............. 62/259.3 |
| 5,415,222 A | 5/1995 | Colvin et al. |
| 5,526,804 A * | 6/1996 | Ottestad .................... 128/201.25 |
| 6,089,226 A | 7/2000 | Gier |
| 6,228,106 B1 * | 5/2001 | Simbruner et al. ............. 607/96 |

(Continued)

OTHER PUBLICATIONS

International Search Report and the Written Opinion of the International Searching Authority, PCT/US05/23449 Dec. 5, 2006.

*Primary Examiner* — Tejash Patel
(74) *Attorney, Agent, or Firm* — Smith Moore Leatherwood LLP; David Krasnow

(57) ABSTRACT

A cooling garment comprises a phase change material and at least one of: at least one leg portion and at least one arm portion. The phase change material may have a transition temperature between solid and liquid phases of between about 60° F. to about 90° F. The at least one arm portion has the phase change material disposed therein, and the at least one leg portion has the phase change material disposed therein. The arm and leg portions may be attached to a torso portion and shorts portion, respectively, and may be removable therefrom. The cooling garment may include a sensor configured to indicate a cooling capacity of the phase change material. A portable container having a reactivation substance stored therein may be provided to reactivate the phase change material. In one embodiment, the portable container is part of a self-contained breathing apparatus. In another embodiment, the phase change material is submerged in the reactivation substance in the container.

29 Claims, 4 Drawing Sheets

U.S. PATENT DOCUMENTS

| | | |
|---|---|---|
| 6,298,907 B1 | 10/2001 | Colvin et al. |
| 6,473,904 B2 * | 11/2002 | Long .................................. 2/2.15 |
| 6,602,277 B2 | 8/2003 | Grahn et al. |
| 6,644,042 B1 | 11/2003 | Robbie et al. |
| 6,656,208 B2 | 12/2003 | Grahn et al. |
| 6,673,099 B2 | 1/2004 | Grahn et al. |
| 6,855,410 B2 * | 2/2005 | Buckley ................... 428/311.11 |
| 6,901,769 B2 * | 6/2005 | Blackstone ..................... 62/420 |
| 6,942,018 B2 | 9/2005 | Goodson et al. |
| 6,966,922 B2 | 11/2005 | Grahn et al. |
| 6,974,442 B2 | 12/2005 | Grahn et al. |
| 7,179,279 B2 * | 2/2007 | Radons et al. ................ 607/108 |

\* cited by examiner

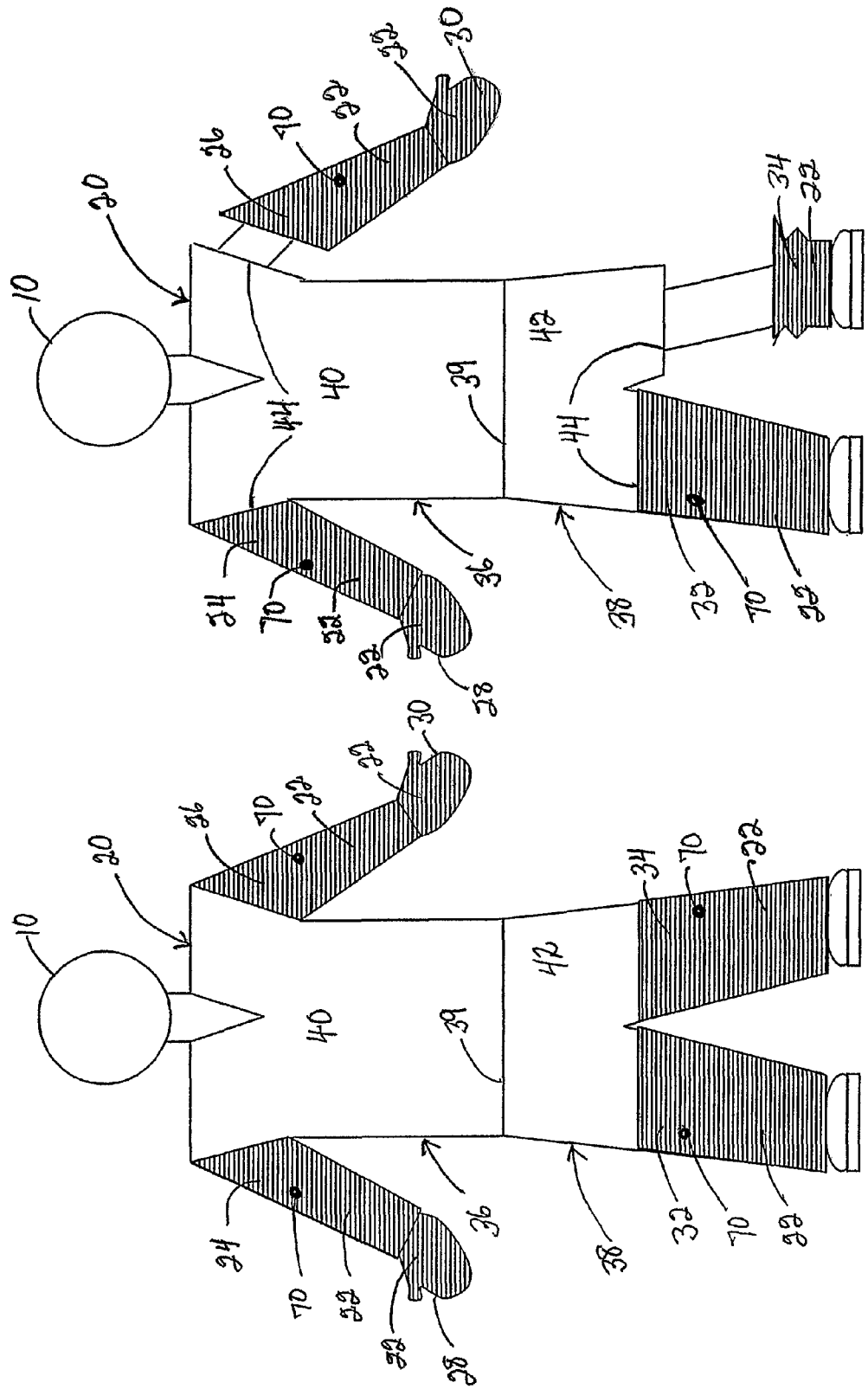

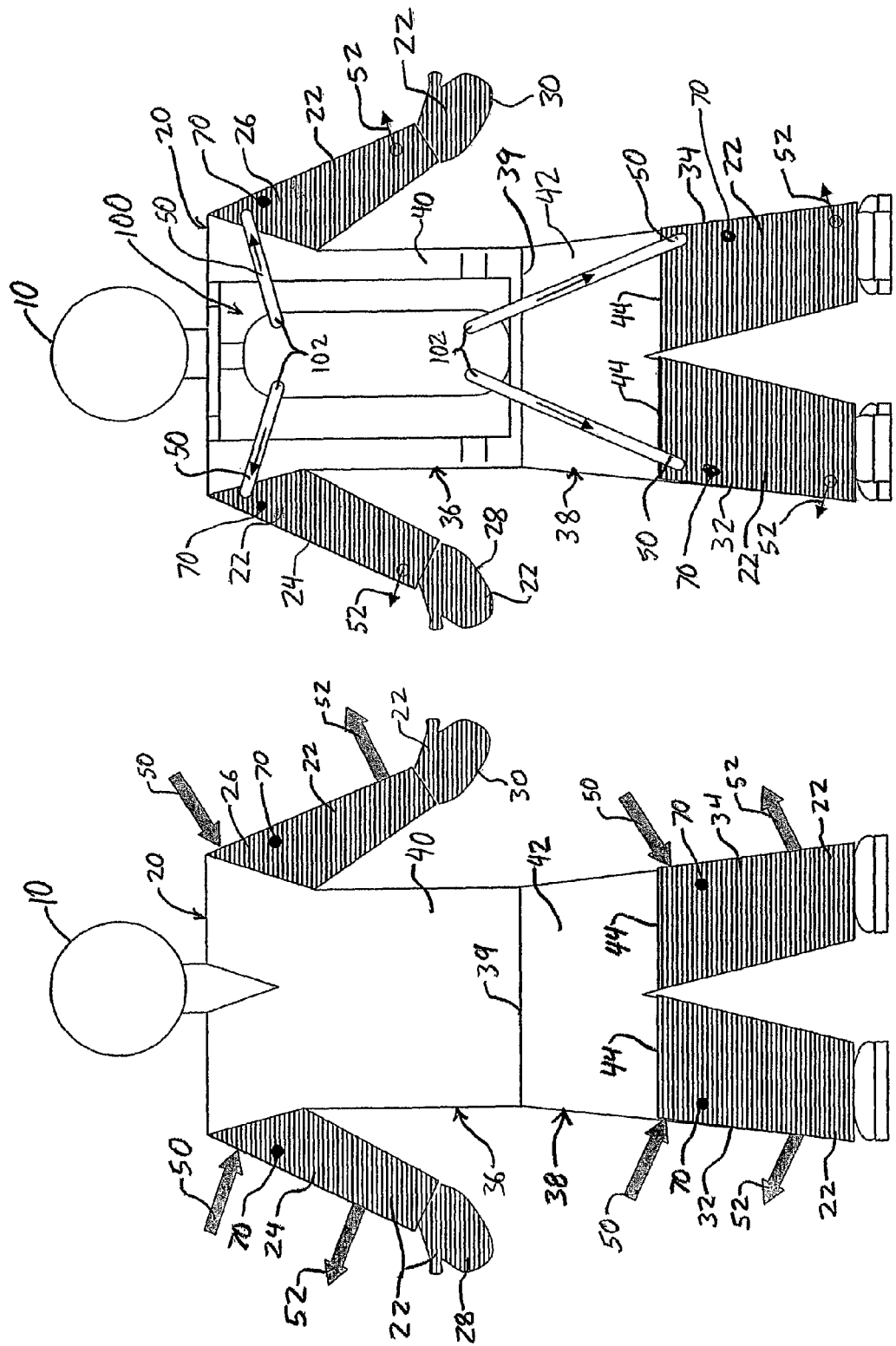

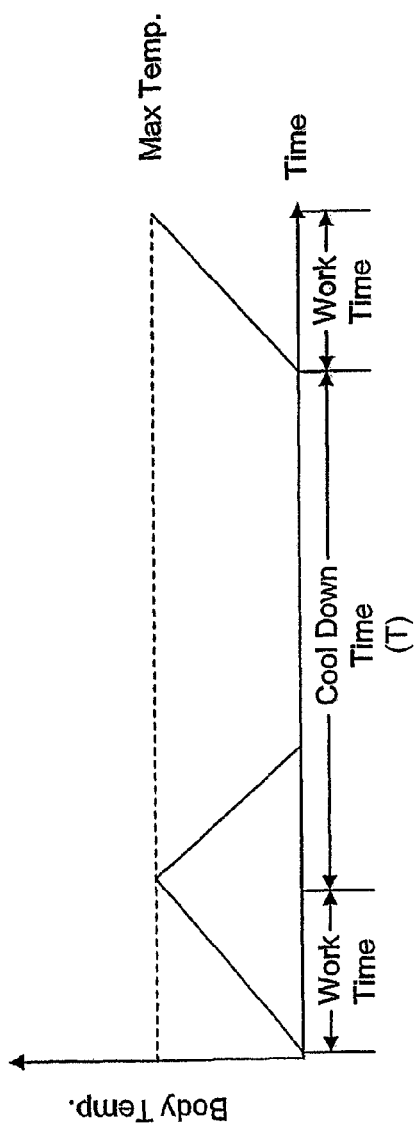
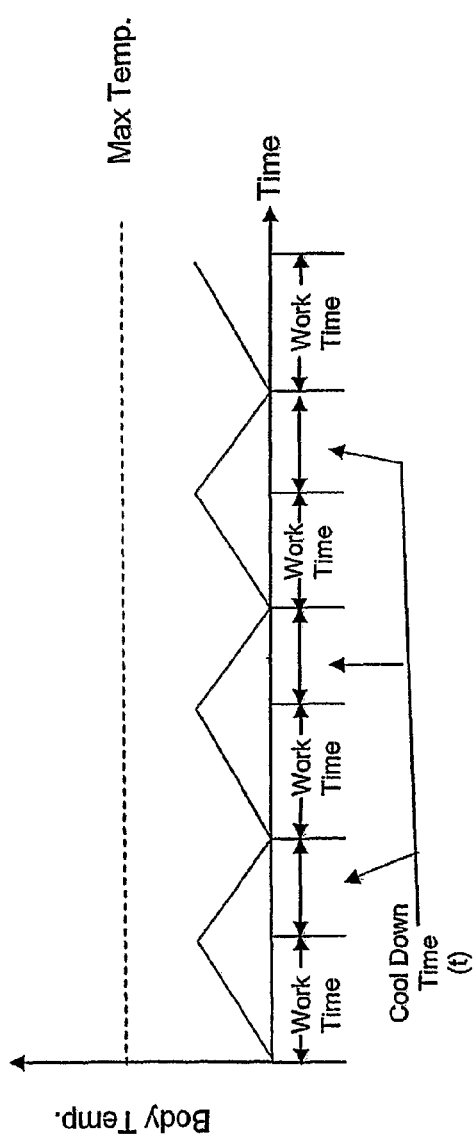

COOLING GARMENT HAVING PHASE CHANGE MATERIAL IN ITS EXTREMITY PORTIONS

CROSS-REFERENCE TO RELATED APPLICATIONS

This application is a continuation-in-part of U.S. application Ser. No. 11/167,324, filed Jun. 27, 2005 now abandoned, which claims the benefit of U.S. Provisional Patent Application No. 60/585,519, filed Jul. 2, 2004, both of which are entitled "COOLING GARMENT HAVING PHASE CHANGE MATERIAL IN ITS EXTREMITY PORTIONS" and both of which are incorporated by reference herein in their entirety.

BACKGROUND (1) Field of the Invention

The present invention generally relates to cooling garments for preventing heat-related illnesses. In particular, the present invention is directed to a cooling garment that includes phase change materials (PCM) positioned at the extremities of the wearer.

(2) Description of the Related Art

Generally speaking, the human body can tolerate cold environments rather well, but is very sensitive to hot environments. The body has a self-cooling mechanism in the form of evaporation of sweat. However, the body's self-cooling mechanism is limited in at least a couple of ways. First, it will only effectively cool the body at or below a certain ambient temperature and at humidity well under 100%. Second, body fluids must be replenished to sustain the self-cooling mechanism.

Heat strain and the more serious condition heat stress refer to the situation when humans are overheated to the degree that the core temperature is increased. Heat stress may result in various harmful physiological effects on the body's functions. If heat stress is combined with hard and stressful work, it may develop into a life-threatening condition known as heat stroke.

To minimize incidents of heat strain, heat stress, and heat stroke, most work areas are air-conditioned and/or individuals are provided with a locally-cooled environment in the form of a cooling garment, e.g., suit or vest, having cool water circulation or equivalent. Active cooling between work periods and air flow through a worker's uniform are additional ways to minimize incidents of heat-related injuries.

Cooling garments such as cooling vests and cooling suits generally include ice or a phase change material as a medium to reduce the user's elevated temperature and, in so doing, transform the cooling material from solid state to liquid state. In order to cope with a heat production of 300 Watts for a duration of one hour, a cooling suit typically has a weight of approximately 3 kilograms. The use of cooling garments may be problematic due to the high extra weight for some applications, difficulties with arranging a good heat transport from the body to the garment, and the time and effort needed to reactivate the garment after use, e.g., half an hour in ice-cold water. In addition, if ice is used for cooling, the vasoconstriction effect by restricting the blood flow counteracts the cooling capacity of ice.

Other approaches toward reducing core temperature relate to increased ambient airflow though the suit to enhance the body's cooling mechanism through sweating. By removing the humid air in the suit, more evaporation of sweat can take place and consequently give the body more cooling. The problem is that to be effective, high airflow of 200-300 liters/minute is needed, and the ambient air temperature must be some gradient below skin temperature. To take that from a portable air cylinder worn by the user (as with a self contained breathing apparatus (SCBA) commonly employed by fire fighters and other first responders) would reduce the duration of the SCBA too much. Wearable air cylinders would not have adequate capacity to support both the cooling and breathing requirements. The alternative of supplied air through a hose would reduce the user's movements and operating range.

Because existing cooling garments often work to insulate a wearer's body, thereby hindering the body's self-cooling mechanisms, existing cooling garments are often not effective for activities that require a high workload or for users that must be covered for protection against heat or harmful substances, e.g., fire fighters and responders to hazardous materials (HazMat) incidents. In these cases, users wearing existing cooling garments may still be subject to overheating and heat-related injuries.

Some products offer cooling of hands and arms after exposure to high heat, thereby reducing the core temperature. However, physiological data indicates that if a person has been exposed to heat stress, there is no way for him to recover in a short time. After the body has been overheated, a rest of days is suggested. Consequently, although some products are effective at quickly reducing the core temperature, they do not reduce the risk of heat stroke if more strenuous work is done the same day or without an appropriate period of rest.

BRIEF SUMMARY

The above-described and other drawbacks and deficiencies of the prior art are overcome or alleviated by a cooling garment comprising a phase change material and at least one of: at least one leg portion and at least one arm portion. The phase change material has a transition temperature between solid and liquid phases of between about 60° F. to about 90° F. The at least one arm portion has the phase change material disposed therein, and the at least one leg portion has the phase change material disposed therein.

In one aspect, there is provided a system comprising a cooling garment and a portable container having a reactivation substance stored therein. The cooling garment includes a phase change material and at least one of: at least one leg portion and at least one arm portion. The phase change material has a transition temperature between solid and liquid phases. The at least one arm portion has the phase change material disposed therein, and the at least one leg portion has the phase change material disposed therein. The reactivation substance has a temperature less than the transition temperature of the phase change material, and the reactivation substance is applied to the phase change material to reactivate the phase change material. In one embodiment, the portable container is part of a self-contained breathing apparatus. In another embodiment, the phase change material is submerged in the reactivation substance in the container to reactivate the phase change material.

In another aspect, there is provided a cooling garment comprising a phase change material and a sensor configured to indicate a cooling capacity of the phase change material.

In yet another aspect, there is provided a cooling garment comprising a phase change material and at least one of a shirt portion and a pants portion. The shirt portion has left and right arm portions removably attached to a torso portion. The phase change material is disposed in the left and right arm portions, and the left and right arm portions are removable from the torso portion. The pants portion has left and right leg portions removably attached to a shorts portion. The phase change material is disposed in the left and right leg portions, and the left and right leg portions are removable from the shorts portion.

BRIEF DESCRIPTION OF THE DRAWINGS

Referring now to the drawings wherein like items are numbered alike in the several Figures:

FIG. 1 is a front view of a worker wearing a cooling garment having phase change material in its extremity portions;

FIG. 2 is a front view of a worker wearing a cooling garment having phase change material in its extremity portions, wherein the extremity portions are detachable;

FIG. 3 is a front view of a worker wearing a cooling garment having phase change material in its extremity portions, wherein a reactivating substance is applied to the phase change material via inlets and outlets in the suit;

FIG. 4 is a rear view of a worker wearing a cooling garment having phase change material in its extremity portions, wherein a self-contained breathing apparatus is arranged to reactivate the phase change material;

FIG. 6 is a typical graph of Body Temperature vs. Cool-Down Time for workers wearing a prior art cooling garment; and FIG. 7 is a typical graph of Body Temperature vs. Cool-Down Time for workers wearing a cooling garment according to various embodiments of the present invention.

DETAILED DESCRIPTION

Figure 5:
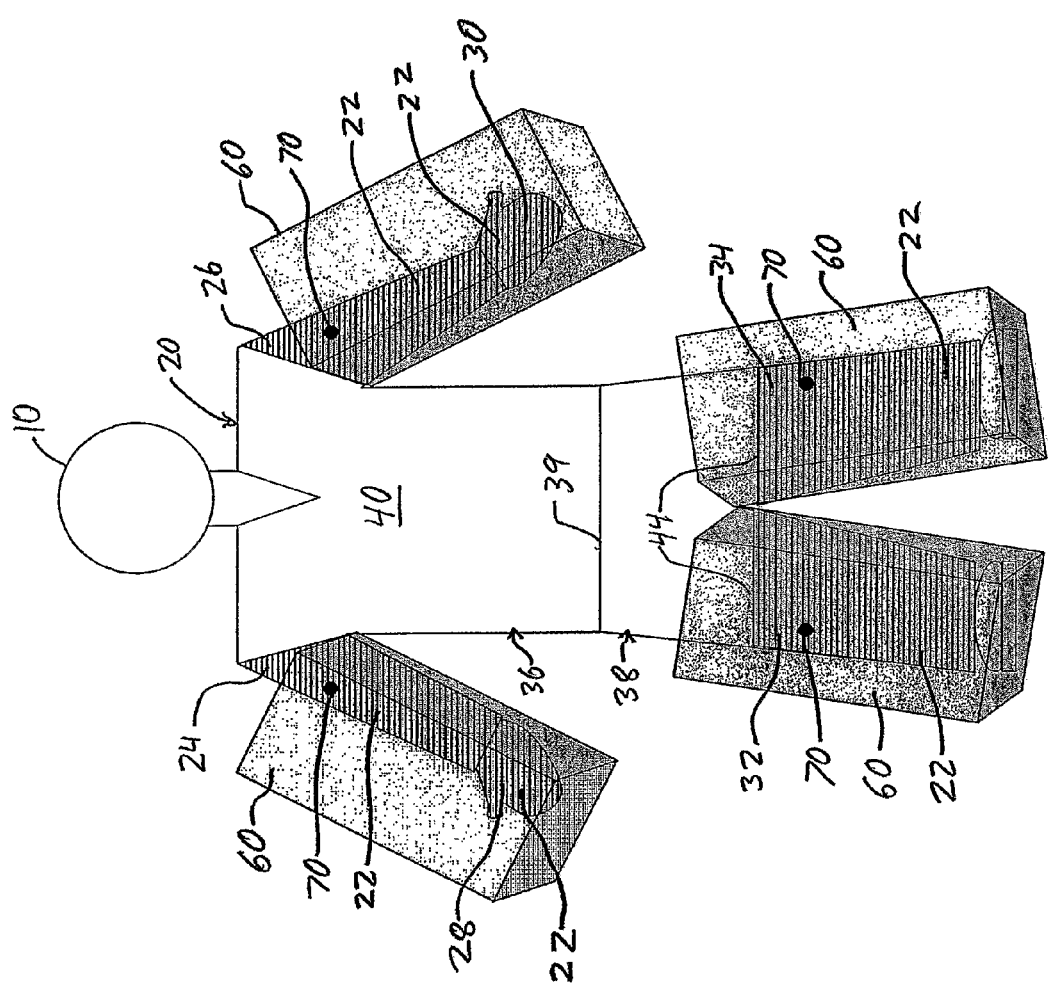
FIG. 5 is a front view of a worker wearing a cooling garment having phase change material in its extremity portions, wherein the extremity portions of the garment are submersed in reactivation substance containers to reactivate the phase change material.

FIG. 1 depicts a front view of a worker 10 wearing a cooling garment 20 having phase change material (PCM) 22 (indicated by horizontal hatching) in its extremity portions, e.g., in the right and left arm portions 24, 26, right and left gloves 28, 30, and right and left leg portions 32, 34. The PCM 22 may be secured within the garment 20 using any convenient means. For example, the PCM 22 may be attached (e.g., sewn, molded, etc.) to the inner portion of the garment 20 such that the PCM 22 is in direct contact to the skin of the worker 10. Alternatively, the PCM 22 may be disposed between two or more layers of material, with the material disposed between the PCM 22 and the worker 10 transferring heat between the worker 10 and the PCM 22. PCM 22 typically will be incorporated in small pads adjacent a wearer's hands, arms, legs, or other places on the body that have good circulation and therefore good heat transfer ability. Typically, the pads will be adapted to make good skin contact with a wearer to increase heat transfer efficiency. While the wearer of the cooling garment 20 is shown as worker 10, it will be appreciated that the garment 20 may be worn for non-work functions as well.

It has been determined by the present inventor that, to provide effective cooling of the worker 10, the cooling garment 20 need only have PCM 22 located at the extremities of the worker 10 (e.g., arms, legs, and/or hands). While not wanting to be bound by theory, it is believed that heat loss through the extremities of the worker 10 is a more efficient process than heat loss through the core (torso) of the worker 10. Metabolic processes in the torso are the main source of heat generation contributing to core temperature elevation, but moderation of that heat is best achieved through radiant and conductive loss through the extremities. Accordingly, the cooling garment 20 having phase change material PCM 22 in its extremity portions is believed to be more effective at cooling the worker 10 than cooling garments having PCM located to cool only the torso of the worker. While the cooling garment 20 need only have PCM 22 located at the extremity portions of the worker 10 to provide effective cooling of the worker 10, it is contemplated that the cooling garment 20 may also include PCM 22 positioned at the torso of the worker 10. However, as will be described in further detail hereinafter, PCM 22 typically requires reactivation and/or replacement at certain time intervals to maintain its effectiveness as a coolant, and a cooling garment 20 having PCM 22 only in its extremity portions provides advantages in quickly and efficiently reactivating or replacing the PCM 22. Furthermore, a cooling garment 20 having PCM 22 only in its extremity portions can provide advantages in quickly and efficiently donning and doffing the garment 20.

As used herein, a phase change material (PCM) is any material which undergoes a phase change from solid to liquid form to provide effective cooling of the surface of the skin of the wearer. For example, PCM 22 may be a bulk paraffin such as that described in U.S. Pat. Nos. 5,415,222 and 6,298,907, both issued to Colvin et al., and both of which are hereby incorporated in their entirety as if fully disclosed herein. Colvin et al. describe a PCM comprising a paraffinic hydrocarbon selected from one or more of n-Octacosane, n-Heptacosane, n-Hexacosane, n-Pentocosane, n-Tetracosane, n-Tricosane, n-Docosane, n-Homeicosane, n-Eicosane, n-Nonadecane, n-Octadecane, n-Heptadecane, n-Hexadecane, n-Pentadecane, n-Tetradecane, and n-TridecanePCM. In another example, PCM 22 may be any of the materials described in U.S. Pat. No. 4,856,294 issued to Scaringe et al., which is hereby incorporated in its entirety as if fully disclosed herein. Scaringe et al. describe a PCM including a material selected from the group consisting of: chloroacetic acid-o-cresol eutectic, tetradecylbenzene, sodium chromate decahydrate, n-octanoic acid, chloroacetic acid-phenol eutectic, acetic acid, a salt mixture of 37% $NaSO_4$, 17% NaCl and 46% water, 1-octadecene, glycerol, n-hexadecane, polyethylene glycol 600, double clathrate of water with tetrahydrofuran and hydrogen sulfide, lithium chloride ethanolate, n-Heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexhydrate, gallium and sodium sulfate decahydrate.

Generally, it is desired that PCM 22 have the following characteristics: a melting temperature under the normal skin temperature, but not as low that the blood flow is restricted; melting temperature that the material at normal room temperature is in solid state or easily can be brought to solid state by dipping it in tap water; a high latent heat to make the pads as lightweight as possible; not poisonous or flammable; and able to withstand high temperatures and chemicals PCM 22 preferably undergoes a phase change (transition) from solid to liquid form at a temperature between about 60°-90° F., and more preferably between about 70°-90° F.

Cooling garment 20 may include a shirt portion 36 and a pants portion 38. Shirt portion 36 includes a torso portion 40 from which right and left arm portions (e.g. sleeves) 24, 26 extend, and pants portion 38 includes a shorts portion 42 from which right and left leg portions 32, 34 extend. Shirt portion 36 and pants portion 38 may be separate portions or may be joined at a wearer's waist 39 to form a one-piece suit (jumpsuit). As illustrated in FIG. 1, right and left arm portions 24, 26 may be permanently joined to torso portion 40 and right and left leg portion 32, 34 may be permanently connected to shorts portion 42. Alternatively, as illustrated in FIG. 1 right and left arm portions 24, 26 and right and left leg portions 32, 34 may be detachably connected to torso portion 40 and shorts portion 42, respectively, using conventional attachment devices 44, e.g., zippers, buttons, snaps, Velcro, etc. In FIG. 2, left arm portion 26 is detached from torso portion 40 and left leg portion 34 is detached from shorts portion 42. It will be appreciated that the right arm portion 24 and right leg portion 34 may be similarly detached. In any of the embodiments, it is contemplated that the shirt portion 36 and pants portion 38 may be used separately.

As used herein, a shirt portion is any garment or portion of a garment that is worn on the upper part of the body. The shirt portion 36 may include a garment that is typically worn as an under-layer (e.g., a tee shirt), a mid-layer (e.g., a sweater), or an outer layer (e.g., a jacket). The shirt portion 36 may also form part of a jumpsuit, which includes a pants portion 38. As used herein, a pants portion is any garment or portion of a garment that is worn on the lower part of the body. The pants portion 38 may include a garment that is typically worn as an under-layer (e.g., underwear), a mid-layer (e.g., trousers), or an outer layer (e.g., chaps or other protective pants). The pants portion 38 may also form part of a jumpsuit, which includes a shirt portion 36

Referring again to FIG. 1, it is also contemplated that the cooling garment 20 may comprise one or more arm portions 24, 26, and/or one or more leg portions 32, 34, without the use of a torso portion 40 or shorts portion 42. In this embodiment, the arm portions 24, 26 may be formed as sleeves, which can be donned by the worker 10 over his or her arms when cooling is needed. Similarly, the leg portions 32, 34 can be donned by the worker over his or her legs when cooling is needed. The arm portions 24, 26 and leg portions 32, 34 may be secured on the worker's arms and legs using elastic straps, belts, and the like. It is also contemplated that each arm portion 24, 26 and leg portion 32, 34 may be wrapped around the arm or leg, respectively, of the worker 10 and secured to itself (and thus on the worker's arms and legs) using conventional attachment devices, e.g., zippers, buttons, snaps, Velcro, etc.

As previously noted, PCM 22 typically requires reactivation or replacement at certain time intervals to maintain its effectiveness in cooling the worker 10. As used herein, to reactivate the PCM 22 means to increase the ability of the PCM 22 to cool the wearer of the cooling garment 20. For example, PCM 22 may be reactivated by changing the state of the PCM 22 from liquid to solid (re-freezing or solidifying the PCM).

In the embodiment of FIG. 2, or where the cooling garment 20 comprises one or more arm portions 24, 26 without a torso portion 40 and/or one or more leg portions 32, 34 without a shorts portion 42, the easy accessibility of the arm portions 24, 26 and leg portions 32, 34 allow these portions to simply be removed should the PCM 22 become deactivated. For example, the worker 10 may doff the right and left arm portions 24, 26 and/or right and left leg portions 32, 34, submerge these portions in a reactivation substance and again don these portions to his or her arms and/or legs. In this way, PCM 22 is reactivated by re-freezing or solidifying the PCM 22. Alternatively, the worker 10 may have replacements for the right and left arm portions 24, 26 and right and left leg portions 32, 34 at the worksite, and the worker 10 simply removes the used portions and installs the replacement portions. In this way, used PCM 22 is replaced with activated PCM 22. In general, these embodiments allow for fast reactivation or replacement of the PCM 22 by doffing only those portions located at the wearer's extremities and donning portions having activated PCM 22.

As used herein, a reactivation substance is any substance that has a temperature less than the PCM's phase change temperature. Reactivation substances include, for example, water, air, a PCM, or similar substances. The term "air", as used herein, includes all breathable gas mixtures containing oxygen.

Referring now to FIG. 3, another embodiment is shown wherein both the right and left arm portions 24, 26 and the right and left leg portions 32, 34 include reactivation substance inlets and outlets, 50, 52. A reactivation substance is pumped into inlet 50 and either around or through PCM 22 and out outlet 52. In this way, PCM 22 may be reactivated either by re-freezing or solidifying the PCM 22.

In the embodiment of FIG. 3, the reactivation substance may be stored in a portable container that can be transported to the work site. For example, as shown in FIG. 4, cold air from a self-contained breathing apparatus (SCBA) 100 carried by the worker 10 may be used as the reactivation substance. The air may be stored in liquid or supercritical form thus providing excess cooling capacity. For example, a supercritical air SCBA such as the SCAMP™ supercritical air mobility pack commercially available from Supercritical Thermal Systems, Inc. of Niwot, Colo. may be used. In such supercritical air SCBA's, air is contained in a cryogenic dewar which replaces the high pressure bottle used by a standard SCBA's. "Supercritical air" refers to air at temperatures and pressures above and beyond the critical point of the air (i.e., the end of the boundary between gas and liquid phases in a phase diagram). In the supercritical condition, the distinction between liquid and gas phases no longer exists. The stored air behaves as a single-phase fluid, with no differential boiling or other separation of constituents and thus no change in chemical composition during storage.

Referring now to FIG. 5, an alternative way to reactivate PCM 22 includes submersion of the material into a container 60 holding a reactivation substance. Each container 60 may be sized to receive those portions of cooling garment 20 having PCM 22. For example, each container 60 may be sized to receive at least one arm and glove containing the PCM 22 and/or sized to receive at least one leg containing the PCM 22. Each container 60 may also be portable, such that it can be transported to the worksite.

In use, the worker 10 may insert the arm, glove, and/or leg portions into the containers 60, thereby reactivating the PCM 22 contained therein. As a practical matter, the worker 10 will find it easier to place arms or legs in a container 60 of reactivation substance than to place his or her whole body or torso into a container 60 of reactivation substance, as would be required with a garment having PCM in its torso portion. The ease of reactivating the PCM 22 via a dip bath of arm and/or leg portions means that the worker 10 may frequently reactivate the PCM 22, thereby increasing the cooling ability of the garment 20 and allowing the worker 10 to work for longer periods.

In any of the above embodiments, reactivation may be achieved via direct contact between the PCM 22 and the reactivation substance or through a thermally conductive means between the PCM 22 and the reactivation substance, such as a layer of the protective garment 20.

With the methods of reactivation discussed with reference to FIGS. 1-5, the worker 10 is required to carry less PCM to the worksite than would be required with prior art arrangements. For example, with the methods of reactivation discussed with reference to FIGS. 1-5, a worker 10 expecting to spend six to eight hours in a high heat stress environment need not carry the equivalent of six to eight hours of PCM 22 to the worksite. Frequent and convenient access to the reactivation substance, whether by dipping arm and/or leg portions in the containers 60 of FIG. 5 or applying the reactivation substance as described with reference to FIGS. 1-4, will restore the PCM cooling performance in a cyclical manner, allowing a 15 to 30 minute supply of PCM 22 to cool for the 6-8 hours required.

Referring again to FIGS. 1-5, the portions of the garment 20 that include PCM 22 may include one or more sensors 70 for detecting a state of the PCM 22. In one embodiment, sensors 70 visibly change colors with respect to the cooling capacity of PCM 22. For example, when PCM 22 is activated (i.e., has capacity to cool the wearer (cooling capacity)), the color of the respective sensor 70 is green and when the PCM is deactivated (i.e., no longer has cooling capacity), the color of the respective sensor 70 is red. This provides a wearer of cooling garment 20 a visual indication of the cooling capacity of the PCM 22 contained in the garment 20.

Sensors 70 may be formed from a temperature sensitive material that changes color in response to the temperature of PCM 22. In another embodiment, each sensor 70 may be an electrical device responsive to a temperature or phase (liquid/solid) change of PCM 22. For example, an electrical device may sense changes in an electrical property (e.g., conductivity, resistance, etc.) of the PCM 22 that is responsive to changes in temperature and/or phase of the PCM 22. Alternatively, or in conjunction with the visual indication, sensors 70 may send a signal, e.g., electronic signal, to the worker 10 and/or a third party, indicating the cooling capacity of the PCM 22 within the cooling garment 20.

It is also contemplated that the reactivation substance may be applied to the PCM 22 in response to a signal from an electrical sensor 70. For example, with respect to the embodiment of FIG. 4, a solenoid valve or other automated valve 102 may control the flow of the reactivation substance (e.g., air or water) to the inlets 50 and/or outlets 52 in the right and left arm portions 24, 26 and/or right and left leg portions 32, 34 in response to a signal from an electronic sensor 70 indicating that the PCM 22 is deactivated. This embodiment is particularly advantageous where the reactivation substance is stored in a portable container (e.g., an SCBA) that is carried by the worker 10.

The cooling garment 20 offers benefits over prior art solutions in preventing heat stress and other heat-related injuries. As mentioned above and illustrated in FIG. 6, prior art solutions often fail to prevent a worker from reaching an elevated body temperature (Tmax). It is believed that this is due, at least in part, to the inability of the wearer to determine whether the PCM still has cooling capacity (i.e., is activated). It is also believed that this is due, at least in part, to the worker's not wanting to spend the time performing an inconvenient reactivation process. As a result of reaching this elevated temperature, a longer cool-down time (T), e.g., several days, is required before the worker may resume work activities.

In contrast, a worker wearing cooling garment 20 having sensors 70 will know when the PCM 22 runs out of cooling capacity (i.e., is no longer activated), and will be able to exit the hot work area to reactivate or replace the PCM 22 before reaching Tmax, as indicated in FIG. 7. As a result, the worker may resume work activities after a much shorter cool-down period (t), e.g., minutes or hours. Moreover, using any of the embodiments in FIGS. 1-5, the worker will be able to quickly and conveniently reactivate or replace the PCM 22. Thus, over a certain time interval, a worker wearing cooling garment 20 will typically be able to conduct work activities over a greater amount of work time than workers using prior art solutions. In embodiments such as those described with reference to FIGS. 4 and 5, where the reactivation substance is stored in a portable container (e.g., an SCBA) that can be transported to the work site, a worker wearing the cooling garment 20 need not leave the worksite as long as there is sufficient reactivation substance in the portable container.

The cooling garment 20 provides the worker 10 with minimal restriction to movements and work. In addition, the cooling garment 20 facilitates the donning, doffing, reactivation and replacement of the PCM 22. Finally, the sensors 70 may provide the worker with a visual indication as to the activation status of the PCM 22. In addition, in at least one embodiment, the activation status of the PCM 22 may be provided electronically to allow alarming of both the worker 10 and a supervisor when the PCM 22 runs out of cooling capacity.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A method for increasing the time a worker may work in a high-temperature environment without risk of heat stroke by decreasing a human core temperature comprising the steps of:
   (a) providing a cooling garment to a garment wearer, said garment comprising at least one removable portion selected from the group consisting of: an arm portion and a leg portion, said portion dimensioned to substantially cover at least part of a human extremity, said portion further comprising an amount of phase change material in each portion, said phase change material able to undergo a phase change from solid to liquid at a temperature of from about 60 to about 90° F.; and
   (b) effecting a phase change in the phase change material from solid to liquid to cool the wearer by effecting heat loss in the wearer's body through the wearer's extremities;
   wherein the garment does not comprise any phase change material in a torso portion of the garment and the phase change material in the removable portion is reactivated quickly once the cooling effect of the removable portion is exhausted.

2. The method of claim 1, further comprising the step of:
   (c) reactivating the phase change material by providing a reactivation substance to the phase change material to reactivate the phase change material.

3. The method of claim 2, further comprising the step of;
   repeating steps b and c as needed to substantially maintain a wearer's core temperature within a preselected temperature range by promoting a heat loss in a wearer's body via the wearer's extremities.

4. The method of claim 1, wherein the arm portion and leg portion is detachable from the garment.

5. The method of claim 1, wherein the phase change material comprises at least one material selected from the group consisting of: n-octacosane, n-heptacosane, n-hexacosane, n-pentacosane, n-tetracosane, n-tricosane, n-docasane, n-homeicosane, n-eicosane, n-nonadecane, n-octadecane, n-heptadecane, n-hexadecane, n-pentadecane, n-tetradecane, n-tridecane and combinations thereof.

6. The method of claim 1, wherein the phase change material comprises at least one material selected from the group consisting of: chloro-acetic acid-o-cresol eutectic, tetradecylbenzene, sodium chromate decahydrate, n-octanoic acid, chloroacetic acid-phenol eutectic, acetic acid, 1-octadecene, glycerol, n-hexadecane, polyethylene glycol, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium and sodium sulfate decahydrate and combinations thereof.

7. The method of claim 1, wherein the reactivation substance is a substance having a substance temperature less than the phase change temperature of the phase change material.

8. The method of claim 1, wherein the reactivation substance is contained in a dip bath.

9. The method of claim 7, wherein the substance temperature is maintained at less than about 90° F.

10. The method of claim 1, wherein the reactivation substance is contained in a portable container and the reactivation substance is directed to the phase change material.

11. A system for increasing the time a worker may work in a high-temperature environment without risk of heat stroke by decreasing a human core temperature comprising:
a cooling garment dimensioned to fit a wearer, said garment comprising at least one removable portion selected from the group consisting of: an arm portion and a leg portion, said portion dimensioned to substantially cover at least part of a human extremity, said portion further comprising an amount of phase change material in each portion, said phase change material able to undergo a phase change from solid to liquid at a temperature of from about 60 to about 90° F.; and
a reactivation substance for reactivating the phase change material;
wherein the phase change material undergoes a phase change from solid to liquid at a temperature of from about 60 to about 90° F. to cool the extremity of the wearer to substantially maintain a wearer's core temperature within a preselected temperature range by promoting a heat loss in a human body via the wearer's extremities, and
wherein the garment does not comprise any phase change material in a torso portion of the garment and the phase change material in the removable portion is reactivated quickly once the cooling effect of the removable portion is exhausted.

12. The system of claim 11, wherein the phase change material is repeatedly reactivated by providing a reactivation substance to the phase change material to reactivate the phase change material.

13. The system of claim 11, wherein the arm portions and leg portions are detachable from the garment.

14. The system of claim 11, wherein the phase change material comprises at least one material selected from the group consisting of: n-octacosane, n-heptacosane, n-hexacosane, n-pentacosane, n-tetracosane, n-tricosane, n-docasane, n-homeicosane, n-eicosane, n-nonadecane, n-octadecane, n-heptadecane, n-hexadecane, n-pentadecane, n-tetradecane, n-tridecane and combinations thereof.

15. The system of claim 11, wherein the phase change material comprises at least one material selected from the group consisting of: chloro-acetic acid-o-cresol eutectic, tetradecylbenzene, sodium chromate decahydrate, n-octanoic acid, chloroacetic acid-phenol eutectic, acetic acid, 1-octadecene, glycerol, n-hexadecane, polyethylene glycol, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium and sodium sulfate decahydrate and combinations thereof.

16. The system of claim 11, wherein the reactivation substance comprises a material substantially maintained at a temperature less than the phase change temperature of the phase change material.

17. The system of claim 11, wherein the reactivation substance is provided at a temperature of less than about 90° F.

18. The system of claim 11, wherein the reactivation substance is contained in a portable container and the reactivation substance is directed to the phase change material.

19. The system of claim 11, wherein the reactivation substance is contained in a dip bath.

20. A cooling garment for increasing the time a worker may work in a high-temperature environment without risk of heat stroke, the cooling garment comprising:
a phase change material able to be quickly and repeatedly reactivated from a liquid state to a solid state by providing a reactivation substance to the phase change material to reactivate the phase change material to substantially maintain a wearer's core temperature within a preselected temperature range by promoting a heat loss in a human body through cooling a wearer's extremities;
wherein the garment does not comprise any phase change material in a torso portion of the garment and the phase change material in the removable portion is reactivated quickly once the cooling effect of the removable portion is exhausted.

21. The cooling garment of claim 20, wherein the phase change material is activated in at least one portion, said portion covering a wearer's extremity, and the phase change material undergoes a phase change from solid to liquid at a temperature of from about 60 to about 90° F. to cool the wearer.

22. The cooling garment of claim 20, further comprising a pants portion comprising detachable leg portions.

23. The cooling garment of claim 20, further comprising a shirt portion comprising detachable arm portions.

24. The cooling garment of claim 20, wherein the phase change material comprises at least one material selected from the group consisting of: n-octacosane, n-heptacosane, n-hexacosane, n-pentacosane, n-tetracosane, n-tricosane, n-docasane, n-homeicosane, n-eicosane, n-nonadecane, n-octadecane, n-heptadecane, n-hexadecane, n-pentadecane, n-tetradecane, n-tridecane and combinations thereof.

25. The cooling garment of claim 20, wherein the phase change material comprises at least one material selected from the group consisting of: chloro-acetic acid-o-cresol eutectic, tetradecylbenzene, sodium chromate decahydrate, n-octanoic acid, chloroacetic acid-phenol eutectic, acetic acid, 1-octadecene, glycerol, n-hexadecane, polyethylene glycol, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium and sodium sulfate decahydrate and combinations thereof.

26. The cooling garment of claim 20, wherein the reactivation substance comprises a material substantially maintained at a temperature less than the phase change temperature of the phase change material.

27. The cooling garment of claim 20, wherein the reactivation substance is contained in a portable container and the reactivation substance is directed to the phase change material.

28. The cooling garment of claim 20, wherein the reactivation substance is contained in a dip bath.

29. The cooling garment of claim 22, wherein the pants portion is attached to a shirt portion.

* * * * *